(12) United States Patent
Lavallee et al.

(10) Patent No.: US 8,337,508 B2
(45) Date of Patent: Dec. 25, 2012

(54) DISTRACTOR SYSTEM

(75) Inventors: Stephane Lavallee, Saint Martin d'Uriage (FR); Christopher Plaskos, New York, NY (US)

(73) Assignee: Perception Raisonnement Action en Medecine, La Tronche (FR)

( * ) Notice: Subject to any disclaimer, the term of this patent is extended or adjusted under 35 U.S.C. 154(b) by 1303 days.

(21) Appl. No.: 11/613,615

(22) Filed: Dec. 20, 2006

(65) Prior Publication Data

US 2007/0219561 A1 Sep. 20, 2007

Related U.S. Application Data

(60) Provisional application No. 60/784,343, filed on Mar. 20, 2006, provisional application No. 60/816,054, filed on Jun. 22, 2006.

(51) Int. Cl.
*A61B 17/88* (2006.01)
(52) U.S. Cl. ...................................... 606/105
(58) Field of Classification Search .................... 606/90, 606/102, 86 R, 87–89, 105; 600/424, 427, 600/428, 407
See application file for complete search history.

(56) References Cited

U.S. PATENT DOCUMENTS

| | | | |
|---|---|---|---|
| 4,501,266 A | 2/1985 | McDaniel | |
| 5,540,696 A | 7/1996 | Booth, Jr. et al. | |
| 5,564,437 A | 10/1996 | Bainville et al. | |
| 5,597,379 A | 1/1997 | Haines et al. | |
| 5,733,292 A | 3/1998 | Gustilo et al. | |
| 5,800,438 A | 9/1998 | Tuke et al. | |
| 5,860,980 A | 1/1999 | Axelson, Jr. et al. | |
| 5,911,723 A | 6/1999 | Ashby et al. | |
| 6,022,377 A | 2/2000 | Nuelle et al. | |
| 6,205,411 B1 * | 3/2001 | DiGioia et al. | 703/11 |
| 6,226,548 B1 * | 5/2001 | Foley et al. | 600/426 |
| 6,285,902 B1 * | 9/2001 | Kienzle et al. | 600/427 |
| 6,385,475 B1 * | 5/2002 | Cinquin et al. | 600/407 |
| 6,551,325 B2 * | 4/2003 | Neubauer et al. | 606/88 |
| 6,575,980 B1 | 6/2003 | Robie et al. | |
| 6,725,082 B2 | 4/2004 | Sati et al. | |
| 6,801,801 B1 * | 10/2004 | Sati | 600/429 |
| 6,923,817 B2 * | 8/2005 | Carson et al. | 606/130 |
| 7,206,627 B2 * | 4/2007 | Abovitz et al. | 600/407 |

(Continued)

FOREIGN PATENT DOCUMENTS

EP 1599140 11/2005

(Continued)

OTHER PUBLICATIONS

U.S. Appl. No. 11/422,832, filed Jun. 7, 2006.

*Primary Examiner* — Kevin T Truong
*Assistant Examiner* — Christopher Beccia
(74) *Attorney, Agent, or Firm* — Kim Krizman LLC

(57) ABSTRACT

According to one aspect of the present invention, a computer assisted orthopaedic surgery system for performing joint replacement or resurfacing surgeries includes a computer that contains software that is adapted to permit an operator of the system to physically evaluate post-operative laxity and stiffness of a joint based on planned implant placement, prior to all cuts being made for at least one side of the joint to accommodate the implant and before components of the implant are installed in the joint, wherein the planned implant placement is measured in terms of a position of at least one virtual implant.

34 Claims, 9 Drawing Sheets

U.S. PATENT DOCUMENTS

| | | | |
|---|---|---|---|
| 7,237,556 B2 * | 7/2007 | Smothers et al. | 128/898 |
| 7,392,076 B2 * | 6/2008 | Moctezuma de La Barrera | 600/427 |
| 7,477,926 B2 * | 1/2009 | McCombs | 600/407 |
| 7,635,369 B2 | 12/2009 | Cinquin et al. | |
| 7,747,311 B2 * | 6/2010 | Quaid, III | 600/424 |
| 2003/0187452 A1 | 10/2003 | Smith et al. | |
| 2004/0171924 A1 * | 9/2004 | Mire et al. | 600/407 |
| 2005/0101966 A1 | 5/2005 | Lavallee | |
| 2005/0197569 A1 * | 9/2005 | McCombs | 600/426 |
| 2005/0251148 A1 * | 11/2005 | Friedrich et al. | 606/88 |
| 2005/0267485 A1 | 12/2005 | Cordes | |
| 2006/0293614 A1 * | 12/2006 | Radinsky et al. | 600/587 |

FOREIGN PATENT DOCUMENTS

| | | |
|---|---|---|
| WO | 2004078047 | 9/2004 |
| WO | 2005018509 | 3/2005 |

\* cited by examiner

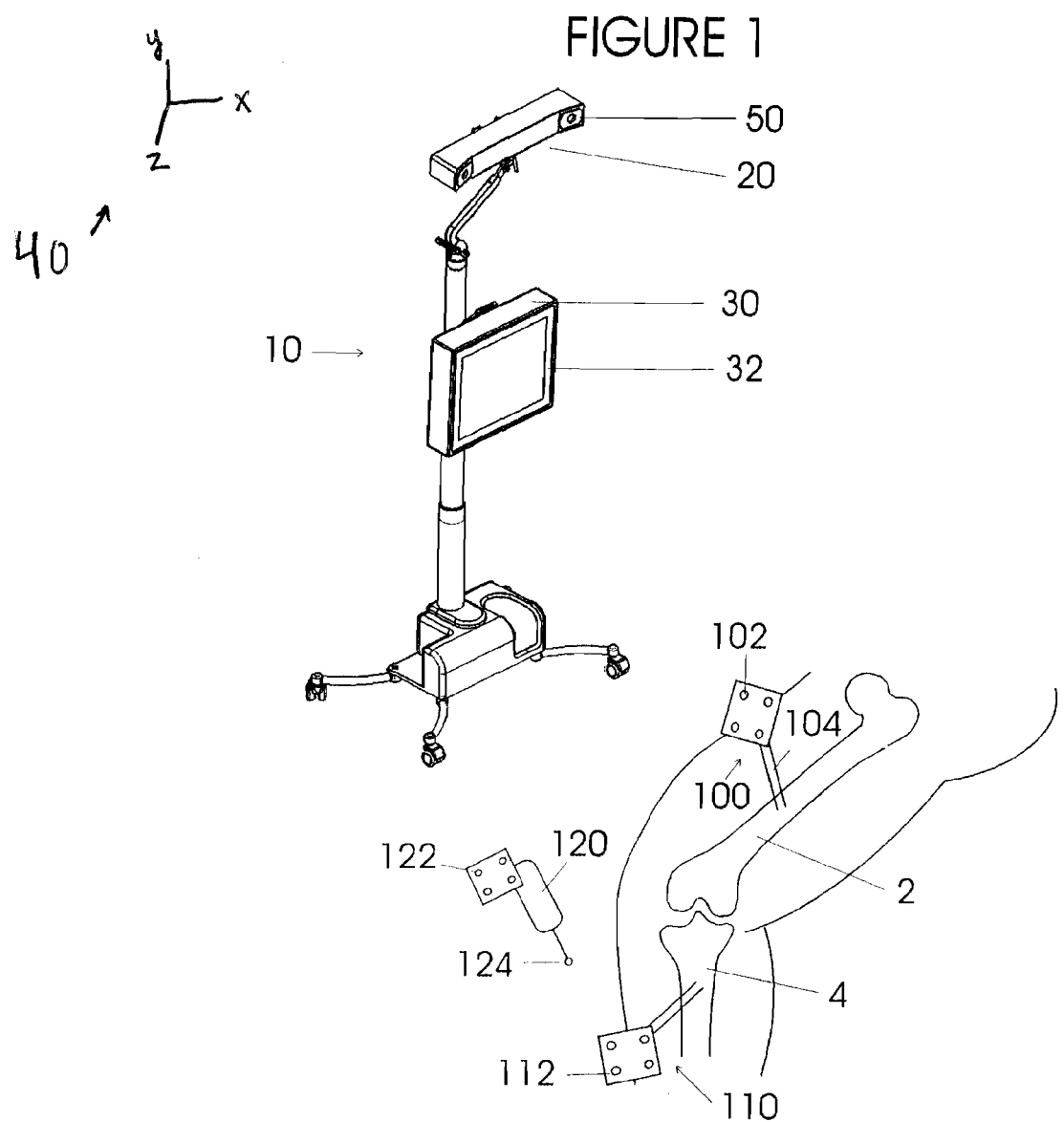

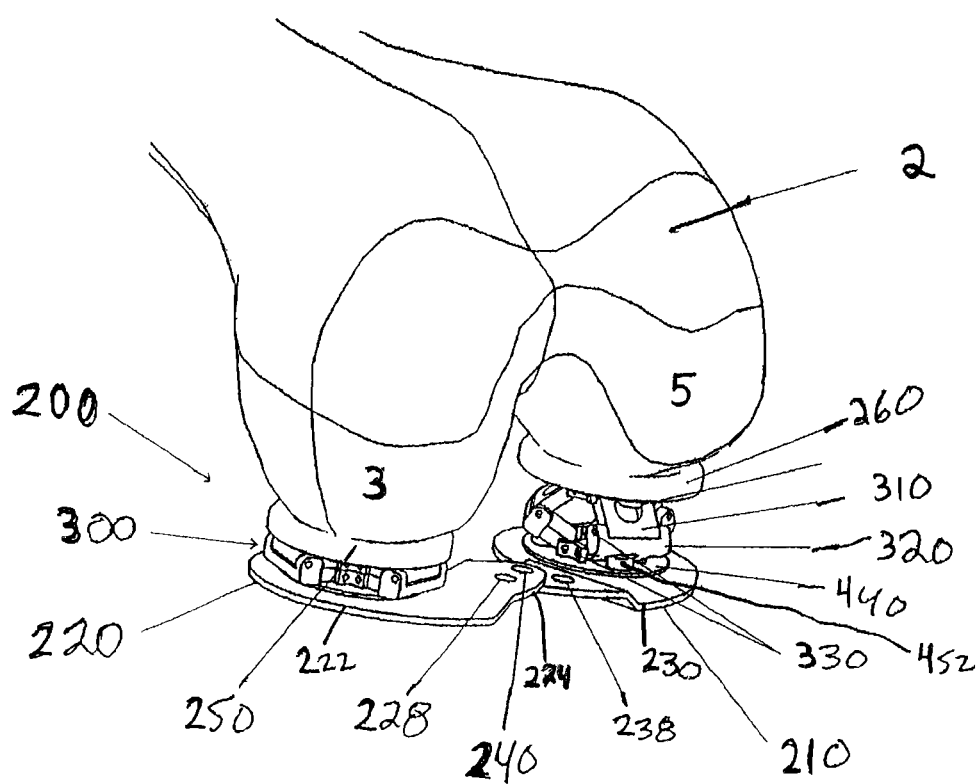
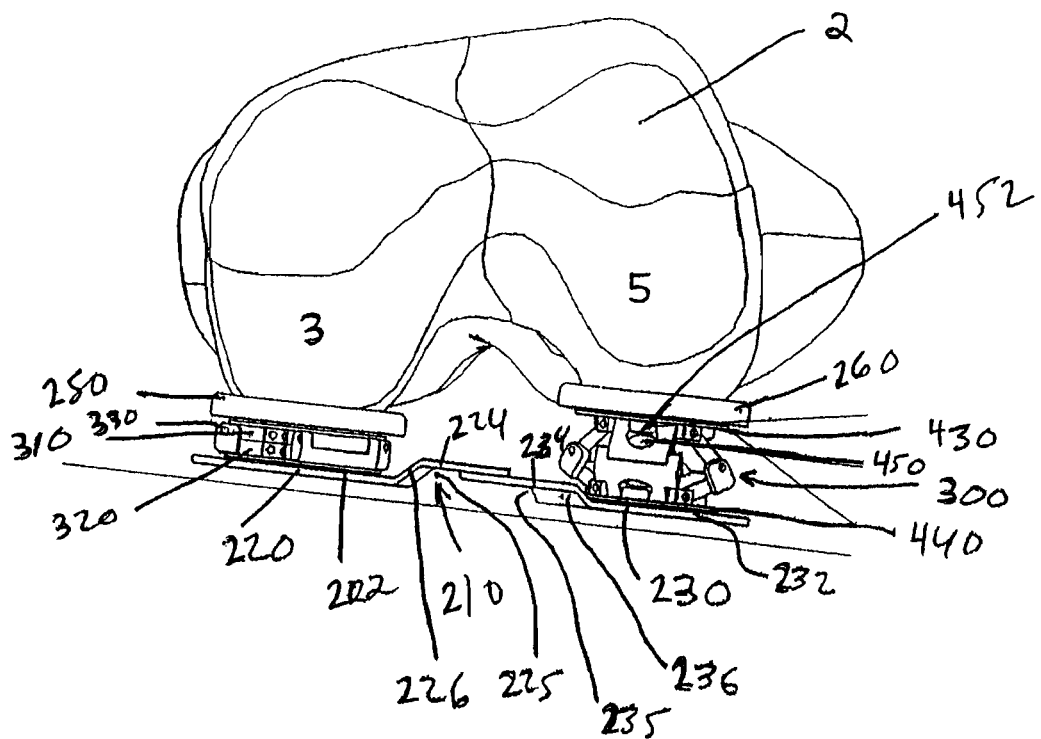

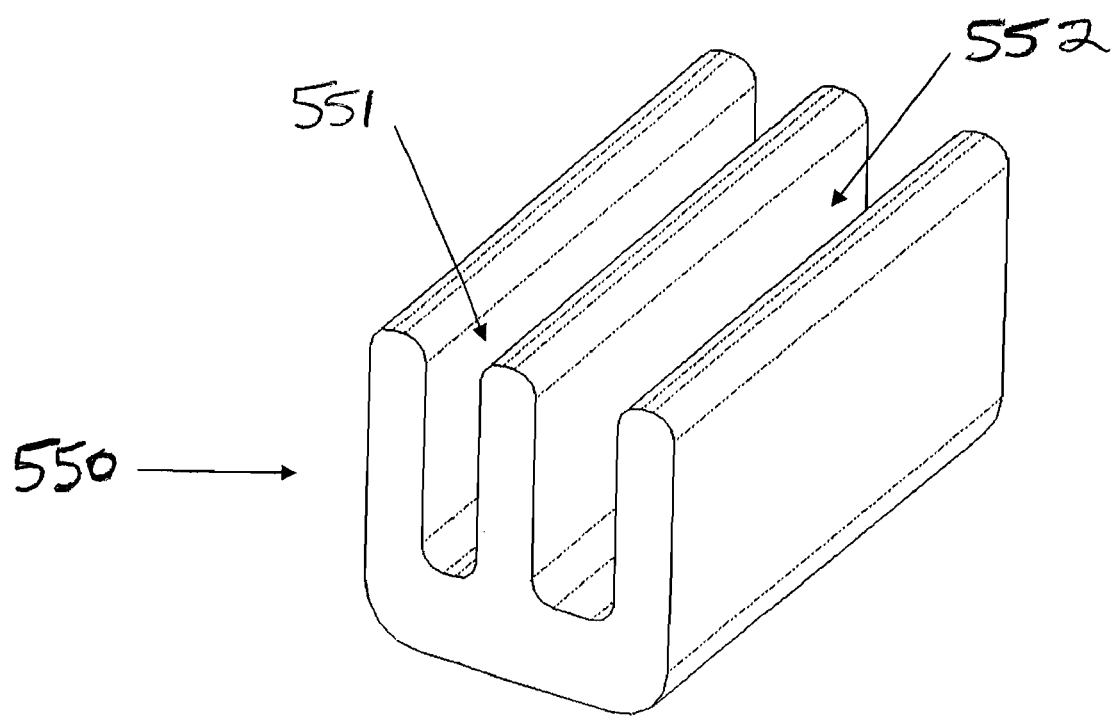

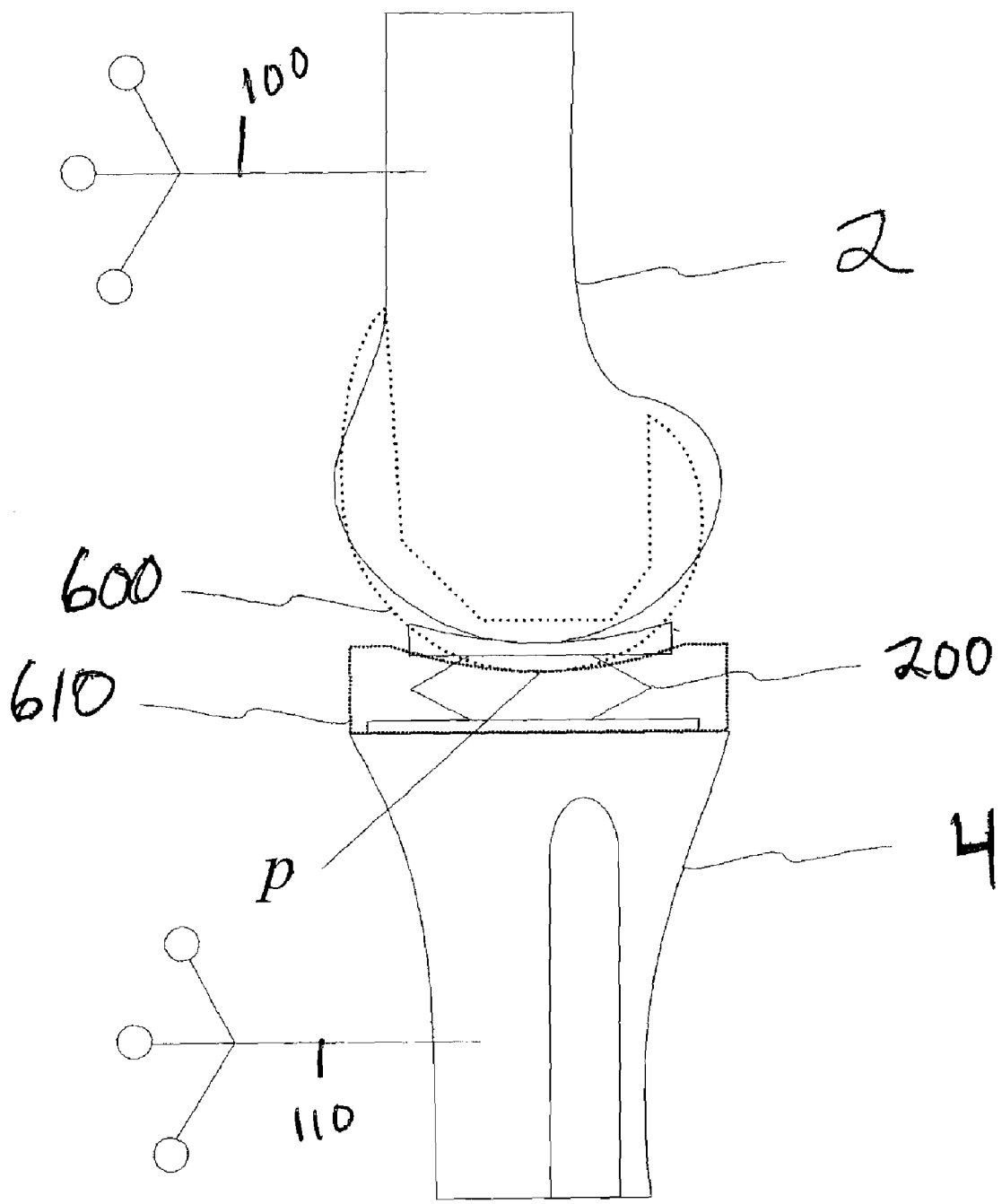

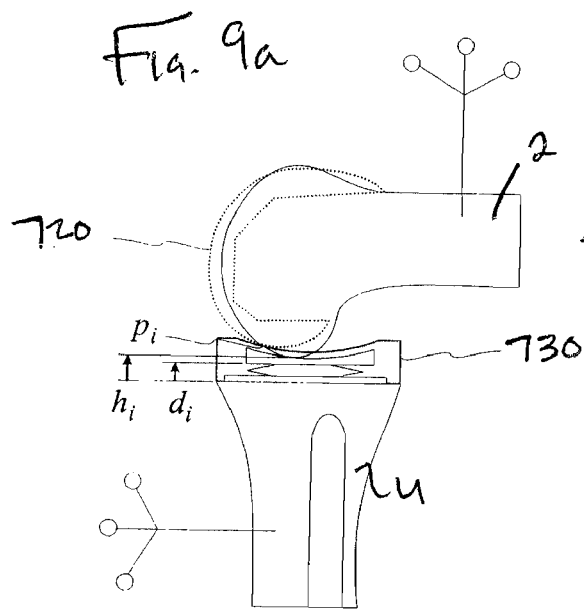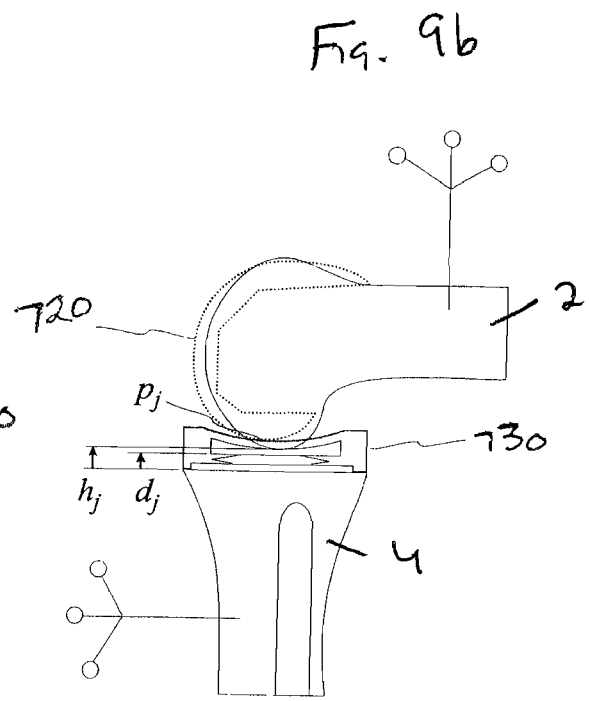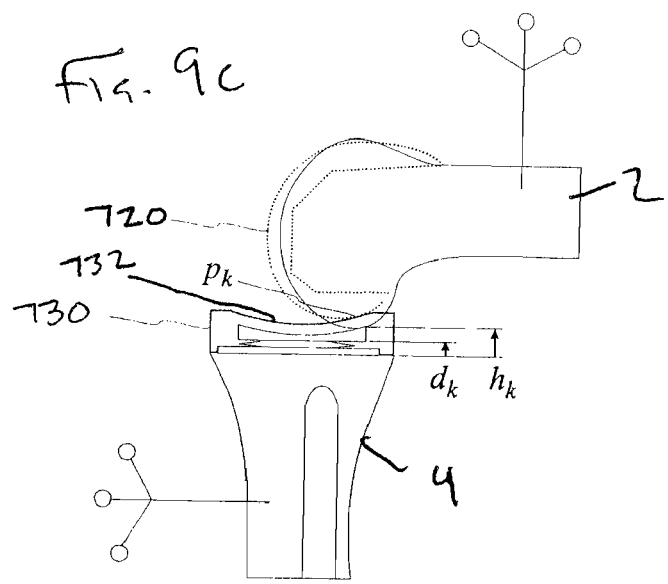

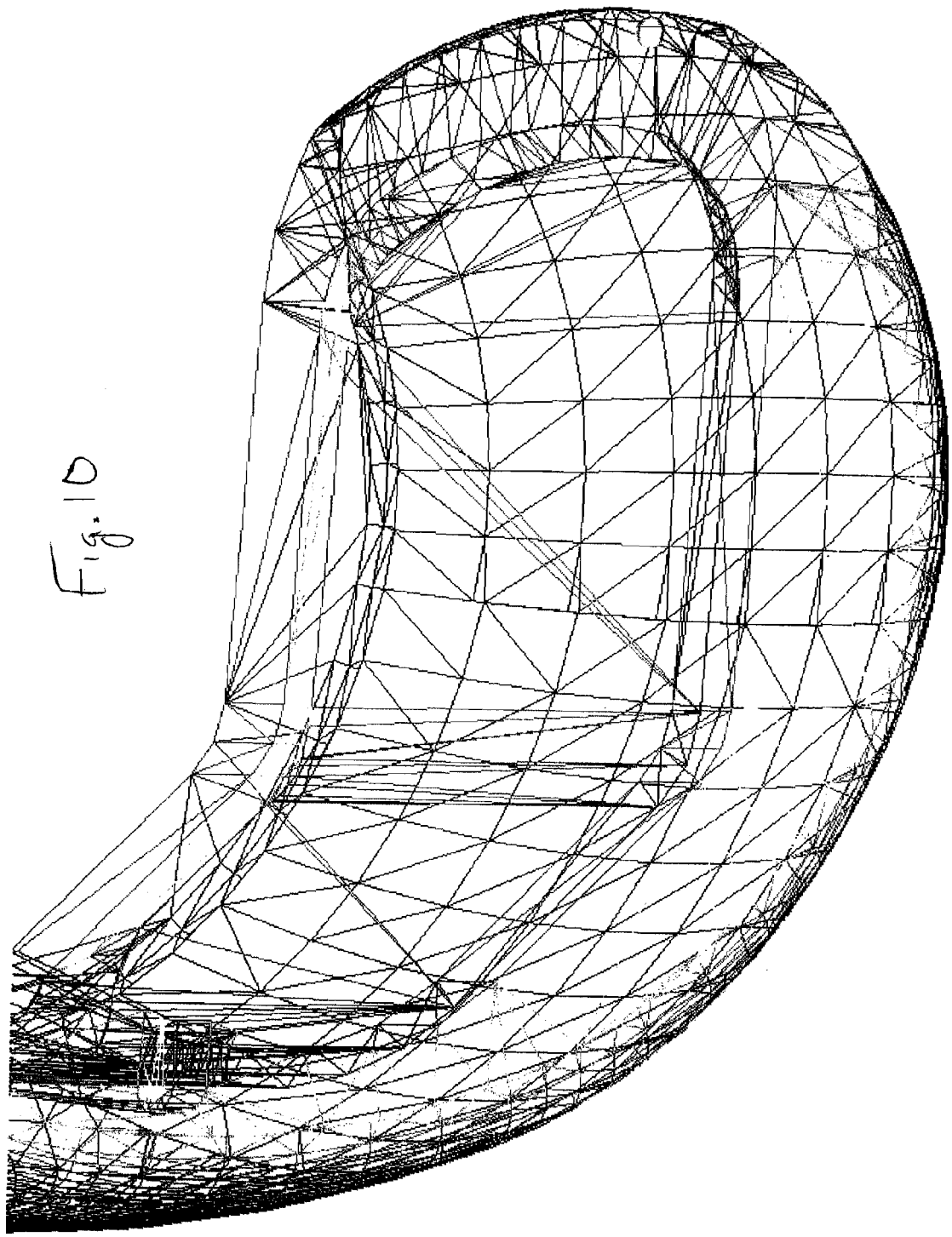

DISTRACTOR SYSTEM

CROSS-REFERENCE TO RELATED APPLICATION

The present application claims the benefit of U.S. patent application Ser. No. 60/784,343, filed Mar. 20, 2006, and U.S. patent application Ser. No. 60/816,054, filed Jun. 22, 2006, each of which is hereby incorporated by reference in its entirety.

TECHNICAL FIELD

The present invention relates to the field of joint replacement or joint resurfacing surgery, and more particularly, to the field of computer assisted joint surgery.

BACKGROUND

The success of joint replacement surgery is primarily dependent on two factors, namely, (1) the position of the implant components with respect to the boney anatomy; and (2) the postoperative state of the surrounding soft tissues. Joints are surrounded by ligamenteous and capsular tissue. The state of these soft tissues determines the laxity and stability of the joint. The state of the soft tissues is effected by the following two factors: (1) the position of the components; and (2) the amount of soft tissue releases performed by the surgeon, as discusses in U.S. patent application publication No. 2005/0267485, which is hereby incorporated by reference in its entirety. In addition, a number of devices and techniques have been described that attempt to facilitate ligament balancing during a TKA procedure and in particular, some of these techniques involve trial prosthesis components which are used after femoral and tibial bone cuts are made to assess ligament tissue. See, U.S. Pat. No. 5,733,292, which is hereby incorporated by reference in its entirety.

Other devices are used to measure a gap between the distal femur and proximal tibia in extension and to help a surgeon recreate that same gap when the knee is in flexion. See, U.S. patent application publication No. 2003/0187452 and U.S. Pat. No. 6,575,980, both of which describe "gap checking" devices, each of which is hereby incorporated by reference in its entirety. Other devices have been developed to help measure an amount of ligament tension or to apply a desired amount of tension to the ligaments and in addition, paddle-like devices have been suggested for applying or measuring tension across a knee joint. See, U.S. Pat. Nos. 4,501,266; 5,597,379; 5,540,696; 5,800,438; 5,860,980; 5,911,723; and 6,022,377, each of which is hereby incorporated by reference in its entirety.

The device described in the above mentioned '485 publication is designed to determine the rotational alignment of the femoral component such that the knee is in optimal tension; however, there are a number of disadvantages and limitations associated with this device. For example, the following are disadvantages associated with this device: (1) the distal femoral cut must be made first before the device is inserted and therefore, one can not change the planning in varus/valgus; proximal/distal, and flexion/extension; (2) the device must be fixed to the femur and therefore, requires bone screws on the medial and lateral sides which add invasiveness to the bone, as well as the soft tissues since access is required to the lateral side of the joint; (3) a vast number of components sizes for the tibia and the femur are still required; and (4) the system has constraints due to it not being able to account for different prosthetic designs using the same components, for example, different degrees of constraint or concavities of the tibial or femoral components.

In conventional surgery, trial reductions are often performed as a final check as to whether or not the final placement of each component of the implant is satisfactory for each specific patient. This step is performed after planning the position of the implants and the bone cuts on the tibia and femur are made. The surgeon temporarily implants a set of so called trial components, which are the same shape and size of the final prosthesis to be implanted, onto the bone cut surfaces and reduces the joint. With the trial components in place, the surgeon can verify that the stability, kinematics, and orientation of the joint are satisfactory by performing a series of tests. If a satisfactory result is not obtained for any of the tests, the surgeon has the option of either performing releases of the soft tissues, or to make one or several re-cuts on the bone in an attempt to adjust the position or the size of the prosthesis. However, this is often not an easy or obvious task because irreversible bone cuts are already made and therefore, the position of the components can only be altered in a limited manner. For example, it is very difficult to increase the size of a distal femoral component or to repair an anterior cut that notches the femoral bone. Correcting the position of the implants after the cuts have already been made can therefore be a time consuming and frustrating process. Soft tissue releases can be made to help compensate for poor component positioning in some cases; however, this is clearly not the optimal solution. Another disadvantage of having to perform trial reductions is that the hospital is required keep several trays of trial components available in the operating room to accommodate all the different sizes and shapes of implants. This increases the cost of the associated surgical instrumentation as well as the cleaning, sterilization and storage costs. The additional clutter around the operating table can also pose logistic issues for the staff.

While there are some systems and methods for determining the position of a knee-joint endoprosthesis, each suffers from a number of deficiencies. For example, U.S. patent publication No. 2005/0251148 to Friedrich et al. discloses a system that determines the femur and tibia by calculating various virtual relative positions of the femur and tibia according to geometrical data of the knee-joint endoprosthesis and to different assumed positions of the tibial part on the tibia and/or of the femoral part on the femur when the knee is straightened and bent, and in which an assumed position in which the virtual relative position of the femur and the tibia when the knee is straightened and bent differs from the spread position in a specified manner is determined as a selected position. However, this system fails to include a control system that includes a device that moves one bone and is linked to a controller to cause controlled movement of the bones during movement of the joint and in view of the measured/calculated information to monitor the virtual relative positions of the femur and tibia.

A system that would therefore allow the surgeon to perform a "virtual" trial reduction before the actual bone cuts are made and without all the required trial components would be of great value.

SUMMARY

According to one aspect of the present invention, a computer assisted orthopaedic surgery system for performing joint replacement or resurfacing surgeries includes a computer that contains software that is adapted to permit an operator of the system to physically evaluate post-operative laxity and stiffness of a joint based on planned implant placement, prior to all cuts being made for at least one side of the joint to accommodate the implant and before components of the implant are installed in the joint, wherein the planned implant placement is measured in terms of a position of at least one virtual implant.

In one exemplary application, the present system is used in a knee replacement surgery and operation of the system includes the steps of: attaching a femoral reference body to the femur; attaching a tibial reference body to the tibia; building models of the femur and tibia; planning a tibial cut in the tibia; making and measuring the tibial cut; planning a tibial implant; registering a planned position of the tibial implant; planning an initial femoral implant based on a femoral model and optionally based on gap measurements; registering planned position of a femoral implant; adjust a size of a distraction device and inserting the distraction device in the joint; measuring the position of the femur relative to the tibia; adjusting the height of the distraction device accordingly and repeating the two above steps. The planned placement for the femoral and tibial implants are determined using virtual femoral and tibial implants that are graphically illustrated on the computer screen for viewing by the surgeon. Once the desired implant locations are determined in view of information received from measurements of the planned virtual implants, then bone cuts are made and the real physical femoral and tibial implants that were simulated by means of the virtual implants are installed in the joint.

In yet another aspect of the present invention, a method is provided for physically evaluating post-operative laxity and stiffness of a joint based on a planned implant placement, prior to cuts being made for at least one side of the joint to accommodate the implant and before components of the implant are installed in the joint. The method includes the steps of selecting a first implant component that is to be associated with a first bone; selecting a second implant component that is to be associated with a second bone; generating a first virtual implant based in part on the selected first implant component and which is representative of the first implant component; generating a second virtual implant based in part on the selected second implant component and which is representative of the second implant component; displaying images of the first and second bones on a screen; displaying the first virtual implant on the screen by superimposing it on the first bone; displaying the second virtual implant on the screen by superimposing it on the second bone; and moving the first bone relative to the second bone over a range of motion while measuring positions of the first and second bones; and controlling the motion of the first bone with respect to the second bone in at least one degree of freedom that results in outer surfaces of the first and second virtual implants being in contact with one another over the range of motion.

Each step of displaying the first and second bones and displaying the first and second virtual implants includes creating a three-dimensional model for the respective object and displaying it on the screen. In addition, the images of the first and second virtual implants are preferably visually distinguished on the screen by either being displayed in a different color from the color of the images of the first and second bones or by displaying the different structures with different levels of transparency.

Other features and advantages of the present invention will be apparent from the following detailed description when read in conjunction with the accompanying drawings.

BRIEF DESCRIPTION OF THE DRAWING FIGURES

The foregoing and other features of the present invention will be more readily apparent from the following detailed description and drawings figures of illustrative embodiments of the invention in which:

FIG. 1 is a perspective view of a computer-assisted orthopedic surgery system and a view of a knee joint defined by a femur bone and a tibia bone;

FIG. 2 is a perspective view a distraction device according to one embodiment relative to the femur bone;

FIG. 3 is a side perspective view of the distraction device of FIG. 2;

FIG. 6 is a perspective view of a calibration tool for calibrating the distraction device of FIG. 2;

FIG. 7 is a side view of a knee joint showing the planned position of a virtual femoral implant, a virtual tibial implant, the femur, the tibia and the distraction device;

Figure 4:
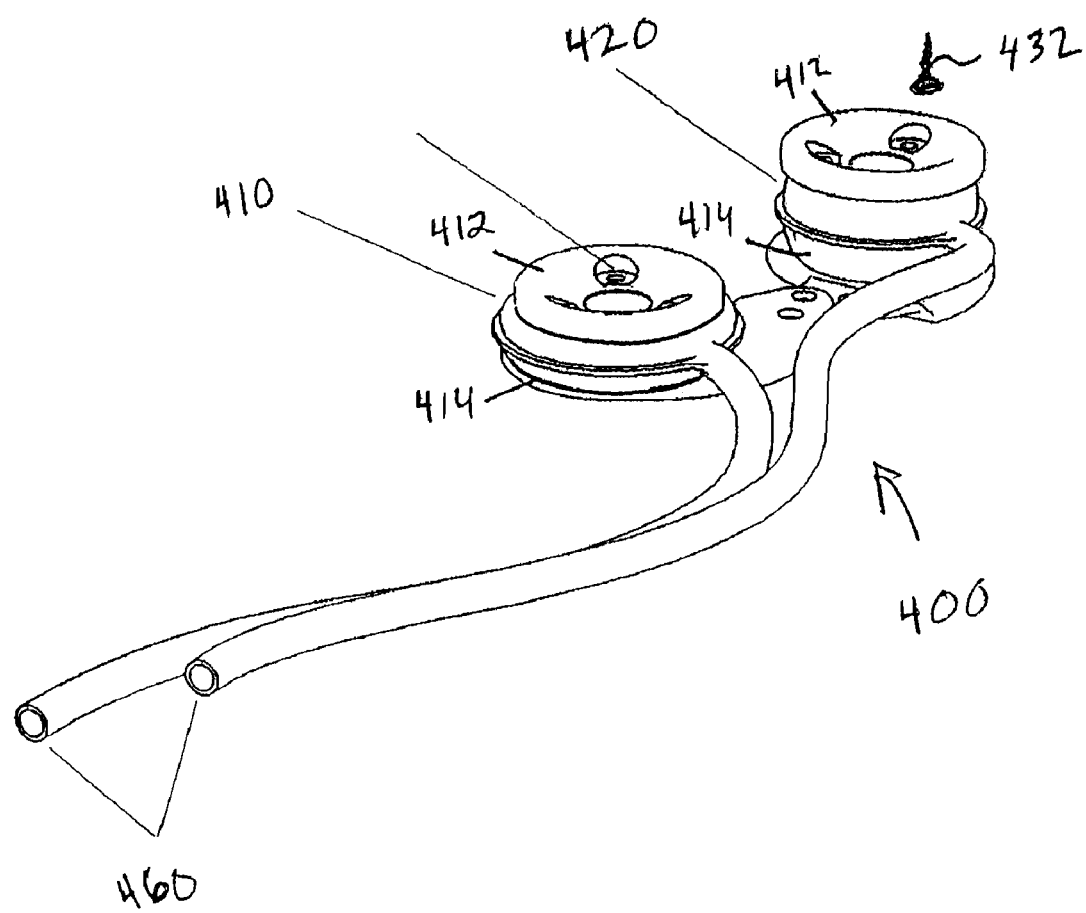
FIG. 4 is a perspective view of one exemplary spacer means for changing the position of the distraction device of FIG. 2.

FIGS. 9a-c are side views of the knee in flexion and being moved in anterior to posterior direction; and FIG. 10 is a schematic view illustrating a geometrical implant file for a femoral implant.

DETAILED DESCRIPTION OF PREFERRED EMBODIMENTS

The following description provides an example of how the present invention can be used in the case of total knee arthroplasty; however, the present invention is not limited to this one surgical application and can be used in any number of other orthopaedic procedures, such as total or partial knee (unicondylar knee replacement), hip, elbow, shoulder arthroplasty or resurfacing.

A system according to the present invention is configured to permit the surgeon to perform a "virtual" trial reduction prior to making all of the bone cuts necessary to insert and accommodate the implant components and in particular, the system and components thereof are used as tools in an overall simulation package that provides virtual simulation to ensure optimal placement of the implant components. The system includes a plurality of components that communication and operate together.

The overall system includes a navigation component (tool) and in particular, a navigation system. Referring now to FIG. 1, a computer-assisted orthopaedic surgery (CAOS) system 10 is schematically shown. The CAOS system 10 is configured for performing joint replacement or resurfacing surgeries, such as knee or hip replacement surgery. The system 10 includes a suitable position measuring device 20 that can accurately measure the position of marking elements in three dimensional space. The position measuring device 20 can employ any type of position measuring method as may be known in the art, for example, emitter/detector or reflector systems including optic, acoustic or other wave forms, shape based recognition tracking algorithms, or video-based, mechanical, electromagnetic and radio frequency systems.

In a preferred embodiment, schematically shown in FIG. 1, the position measuring system 20 is an optical tracking system that includes at least one camera that is in communication with a computer system 30 and is positioned to detect light reflected from a number of special light reflecting markers, spheres or discs 50.

Detecting and determining the position and orientation of an object is referred to herein as "tracking" the object. To provide precision tracking of objects, markers 50 can be rigidly connected together to form reference bodies, (e.g., 100, 110), and these reference bodies can be attached to bones, tools and other objects to be tracked. One such device that has been found to be suitable for performing the tracking function is the Polaris™ system from Northern Digital Inc., Ontario, Canada. However, other systems can be used also.

The position measurement device 20 is described in greater detail in a number of publications, including U.S. Pat. Nos. 5,564,437 and 6,725,082, both of which were previously incorporated by reference.

The position of the patient's bones, such as the patient's femur 2 and the patient's tibia 4, can be determined and tracked by attaching reference bodies 100, 110, which include respective markers 102,112, to the bones 2, 4, respectively. The reference bodies can be attached to bones or tools using pins or screws 104, 114, or various quick release mechanisms. The reference bodies can also be shaped in the form numbers (e.g., "1", "2", "3" . . . ) or alphabetical letters, such as "F" for Femur, "T" for Tibia, "P" for pointer, and so on, so as to avoid confusion as to which reference body should be attached to which bone or tool.

The tracked objects and their relative positions can be displayed on a screen (display) that is connected to the computer system 30. In a preferred embodiment, the display is a touch screen which can also be used for data entry.

The position measurement device 20 includes a number of different tools that are used at different locations and perform different functions as the system 10 is operated to yield optimal joint reconstruction data and information. These tools include a pointer 120, with markers 122, which can be used to digitize points on the surfaces of the femur 2 and tibia 4.

The reference bodies 100, 110, can be used for determining the position and orientation of an individual's bone in a three dimensional coordinate system 40. The reference bodies 100, 110 are preferably rigid and the respective markers 102, 112 are preferably configured to reflect infrared light. Markers 102, 112 are sufficient to establish the position and orientation of the rigid bodies 100, 110 within the coordinate system 40.

Using the computer navigation station 10 and the associated tools and reference bodies 100, 110, the surgeon can build or register surface models of the bones of the involved joint. Models of the joint can either be built using point based methods, image-free morphing based methods, or medical image-based methods, such as those described in United States patents and U.S. Pat. No. 6,385,475 to Cinquin et al, US20050101966 to Lavallee, and U.S. Pat. No. 6,205,411 to DiGioia et al. The surgeon can plan the position and the size of the implants to be installed based on these bone models, taking into account many parameters, such as the patents' kinematics, boney anatomy, and soft tissue envelope, etc., or any other methods known in the state of the art, including those described in the abovementioned patents, which are hereby incorporated by reference in their entirety.

Once an appropriate tibial cutting angle and depth has been determined, the tibial cut can be made and the real final cut angle of the bone cut can be measured as is done today using standard techniques and practices. A distraction device can then be then inserted into the joint space in order to distract or to manipulate the femur 2 relative to the tibia 4. Such distraction devices are commonly used and known in the state of the art (see, for example, EP1599140 to Cinquin et al. and WO2005018509 to Briard et al., which are hereby incorporated by reference in their entirety). They can either be outside or inside of the joint.

According to one embodiment of the present invention, the simulation package includes the use of a distraction device 200 illustrated in FIG. 2 and described in greater detail in commonly assigned U.S. patent application Ser. No. 11/422,832, which is hereby incorporated by reference in its entirety. This device 200 is compatible with minimally invasive procedures, where the patella is not reflected and the knee joint is not opened completely.

The distraction device 200 has a flat/planar base 210 which is configured and intended to rest or sit on a plateau cut that is made in a bone as part of the implant surgery. For purposes of illustration only, the distraction device 200 will be described as being used in a knee implant operation and thus FIG. 1 shows a femur bone 2 and tibia bone 4; however, the potential applications of the distraction device 200 extend and go beyond the knee implant surgery and thus, the following description of the application of the distraction device 200 in knee implant surgery is merely exemplary and not limiting of the present invention. In the case where the distraction device 200 is used in knee implant surgery, the base 210 thereof rests on a tibial plateau cut that is made near the end of the tibia 4.

The base 210 is configured so that it is adjustable to accommodate a range of knee sizes. More particularly, the base 210 is in the form of a plate and more specifically, the base 210 is informed of two base plates, namely, a first plate 220 (internal plate) and a second plate 230 (external plate). The first and second plates 220, 230 are adjustable relative to one another and in particular, the first and second plates 220, 230 are pivotably connected to one another by a pivot joint 240. In order for the first and second plates 220, 230 to lie in the same plane and be pivotally connected, the first plate 220 has a main portion 222 and a raised portion 224 that is connected to the main portion 222 by means of a ramp 226. As illustrated in FIG. 2, when the lower surface of the main portion 222 rests on the ground, the portion 224 is elevated relative to the ground such that a space 225 is formed under the lower surface of the raised portion 224. Similarly, the second plate 230 has a main portion 232 and a raised portion 234 that is connected to the main portion 232 by means of a ramp 236. As illustrated in FIG. 2, when the lower surface of the main portion 232 rests on the ground, the portion 234 is elevated relative to the ground such that a space 235 is formed under the lower surface of the raised portion 224.

The first and second plates 220, 230 are pivotally connected at the raised portions 224, 234 and as shown in Pig. 2, one raised portion (e.g., portion 224) overlies the other raised portion (e.g., portion 234). The pivot joint 240 extends through both of the raised portions 224, 234 and permits the two plates 220, 230 to pivot at the raised portions 224, 234 thereof. The raised portion 224 of the first plate 220 has an opening 228 formed therethrough proximate the pivot joint 240. Similarly, the raised portion 234 includes an opening or slot 238 proximate the pivot joint 240. A U-shaped piece (not shown) can be inserted into opening 228 and slot 238. By turning a nut (not shown) or the like that is part of a threaded post of the U-shaped piece that traverses the slot 238, the size and arrangement of the base 210, and in particular, the relative positions of the first and second plates 220, 230 can be locked into a fixed position. Since the portions 224, 234 are raised relative to the main portions 222, 232, respectively, receiving an object (e.g., the U-shaped piece) through the opening 228 and slot 238 does not interfere with the main portions 222, 232 resting on the planar cut since it can be received in the space 225, 235.

The lower surfaces of the first and second base plates 220, 230 can be rough or can have protrusions, such as spikes, so as to prevent the distraction device 200 from sliding around on the tibial plateau cut. In addition, openings can also be included so that the surgeon can fix the distraction device 200 to the tibial bone (at tibial cut) by means of pins or screws that are received through openings formed through the first and second plates 220, 230.

The distraction device 200 includes two upper femoral plateaus, namely, a first upper femoral plateau member 250 (internal) and a second upper femoral plateau member 260 (external). The first upper femoral plateau member 250 is configured and intended to support the internal (medial) condyle 3 of the femur 2, while the second upper femoral plateau member 260 is configured and intended to support the external (lateral) condyle 5 of the femur 2.

As described above in more detail and based on the pivoting action between the plates 220, 230, the distance of separation between each plateau members 250, 260 is adjustable. More specifically, the optimal distance of separation between the plateau members 250, 260 can be automatically computed from the femoral bone model, by for example, calculating the distance between the most posterior or most distal points on the femoral condyles 3, 5. An average of these two distances can be selected so that the distraction device 200 fits the femur 2 when the knee is in both flexion and in extension. Markings can be incorporated onto the distraction device 200, for example, on the base 210 (plates 220, 230) to indicate the separation distance so that the surgeon can adjust the tibial base distance to the appropriate value as determined by various techniques. Alternatively, a caliper system or similar tool can be used to measure the distance between the plateau members 250, 260. Alternatively, pair of holes can be made in the base plates 220, 230 of the distraction device 200 corresponding to predefined discrete distance that correspond to various sizes of a knee implant. The surgeon can then easily insert a peg or the like into the proper holes in order to replicate a particular size of the implant that corresponds to the planned implant size.

An upper surface of each of the first and second femoral plateau members 250, 260 is constructed to support and complement the respective condyle and can be convex in form in both the sagittal and frontal planes to better fit with the femoral condyles 3, 5, respectively. Thus, they can be spherical or they can have different curvatures in the different planes to simulate different levels of constraints.

The first and second upper femoral plateau members 250, 260 are coupled to the first and second base plates 220, 230, respectively, by means of a linkage mechanism 300 that ensures that each of the plateau members 250, 260 remains parallel to the respective lower base plate 220, 230 throughout the course of the distraction motion (i.e., the range of motion of a distraction operation).

The linkage mechanism 300 is formed of a plurality of link pairs 310, 320 connected to each other and coupled to one of the femoral plateau members 250, 260 and the respective base plate 220, 230 by pins or the like 330. As shown, the link 310 is connected at one end to one of the femoral plateau members 250, 260 and is connected at its other end to one end of the other link 320. The pins 330 permit pivoting of the links 310, 320 with respect to each other and with respect to the femoral plateau plates 250, 260 and the base plates 220, 230.

The links 310, 320 are arranged at angles to each other such that when one pair of links 310, 320 hinges or pivots open, all other link pairs 310, 320 open at an equal angle, thereby constraining the first and second upper femoral plateau members 250, 260 to remain parallel to the first and second lower base plates 220, 230.

In one exemplary embodiment, at least three linkage mechanisms 300 for each of the first and second femoral plateau members 250, 260 and the respective base plate 220, 230 are chosen to optimize the stability, strength and size of the linkage mechanism 300. However, it will be appreciated that each mechanism 300 can have more or less than three pairs of links 310, 320. Thus, two or four pairs of links 310, 320 can be used.

It will also be appreciated that instead of having link pairs defined by parts 310, 320 that are coupled to and between the first and second femoral plateau members 250, 260 and the respective base plate 220, 230, there can be more than two links in each set. In other words, link triplets defined by three link members pivotally attached to one another and to the first and second femoral plateau members 250, 260 and the respective base plate 220, 230 can be provided or link quadruplet defined by four link members can be employed instead of the illustrated link pairs 310, 320. The illustrated linkage mechanism 300 has been designed such that it has a low profile height on the order of about 5 mm when fully retracted as illustrated in FIG. 2, and a considerably higher height of about 15 mm or 20 mm when fully extended. If additional heights are required beyond the maximum height range, spacer blocks can be fastened onto the first and second upper femoral plateau members to augment the maximum achievable height.

The fastening mechanism that is incorporated into the distraction device 200 can be any number of different types, including but not limited to, a quick-clip or snap type mechanism, or a peg and hole type mechanism, or a sliding dove tail joint arrangement, etc. In addition, in the case where the above mentioned spacer blocks are used, these blocks can have similar surfaces to those of the first and second femoral plateau members 250, 260 and are constructed to mate in a complementary manner with the condyles 3, 5 of the femur 2. Alternatively, the spacer blocks can have different shaped surfaces, such as flat planes so that they can fit the femur 2 after the distal femoral and posterior femoral cuts are made. By measuring the gap spaces between the femur 2 and tibia 4, the physician can determine if the required distraction height is greater than the maximum height achievable by the distraction device 200. The system can also advise the surgeon as to which height of spacer block to use in order to sufficiently augment the distraction height, while keeping the distraction device's dynamic range of motion or workspace in a suitable location.

The height of each of the first and second upper femoral plateau members 250, 260 is preferably independently controlled by a controller or some other type of mechanism. There are any number of different techniques that can be used to control the movement of the first and second upper femoral plateau members 250, 260 relative to the first and second base plates 220, 230. For example, the height can be controlled by a hydraulic system. Since the height of the distraction device 200 can be readily changed, the portion of the device 200 that is inserted into the joint can remain as small as possible, and require only a minimum opening of the joint.

FIG. 4 illustrates one exemplary means 400 for controlling the height of the first and second upper femoral plateau members 250, 260 relative to the first and second base plates 220, 230. The illustrated means 400 is a fluid based system and includes a first fluid holding member that is expandable (first pouch) 410 that is intended to be associated with one of the linkage mechanisms 300 and a second fluid holding member that is expandable (second pouch) 320 that is intended to be associated with another linkage mechanism 300. More specifically, the first pouch 410 is constructed to surround one linkage mechanism 300 and receive and hold a fluid (e.g., water) and the second pouch 420 is constructed to surround another linkage mechanism 300. The first pouch 410 is thus a flexible member that has a hollow interior 310 that is constructed to accommodate the linkage mechanisms 300 which in the illustrated embodiments is defined by three pairs of links pairs.

Each of the first and second pouches 410, 420 has an upper part 412 and an opposing lower part 414, with the upper part 412 being coupled to a first intermediate plate 430, while the lower part 414 is coupled to a second intermediate plate 440. The intermediate plates 430, 440 can have any number of different sizes and shapes so long as they are complementary to the other parts and perform the function of providing a mounting surface or substrate that permits the linkage mechanism 300 to be mounted between the base 210 and the upper femoral plateau members 250, 260. In the illustrated embodiment, the intermediate plates 430, 440 are in the form of disks or the like.

In fact, the linkage pairs defined by parts 310, 320 are disposed between the two intermediate plates 430, 440, with the part 310 being attached to the first intermediate plate 430 and the part 320 being attached to the second intermediate plate 440.

The upper part 412 of the first pouch 410 can be coupled to the first intermediate plate 430 with fastening means 432 (such as screws or the like) and the lower part 414 can be coupled to the second intermediate plate 440 with fastening means 432, with the plates 430, 440 being attached to the first upper femoral plateau member 250 and the base plate 220. Similarly, the upper part 412 of the second pouch 420 can be coupled to the first intermediate plate 430 with fastening means 432 (such as screws or the like) and the lower part 414 can be coupled to the second intermediate plate 440 with fastening means 432, with the plates 430, 440 being attached to the second upper femoral plateau member 260 and the base plate 230. The attachment of the first and second pouches 410, 420 to the intermediate plates 430, 440 forms a tight waterproof seal.

Openings 450 formed in the linkage mechanisms 300 prevent hole bosses 452 from interfering and impinging upon the links 310, 320 through the course of the range of distractor motion. In other words, as the distraction device 200 moves over its range of motion (up and down) the screw bosses 452 will likewise move; however, the openings 450 are formed in the links 310, 320 to permit reception of the screw bosses 452 and therefore, permit smooth movement of the device 200.

The pouches 410, 420 can be made out of a medical grade plastic or PVC or any other suitable material. Preferably, the pouches 410, 420 are made from a material that is the least extensible as possible so that the distraction height does not change significantly when loads are applied. The material should be bendable to accommodate changes in the shape as the plateau height is increased or decreased, but should also resist expanding or stretching like a balloon when the fluid pressure increases. In other words, if the fluid volume in the pouches 410, 420 is held constant, the distraction height should also remain constant even if the loads are applied since the pouches 410, 420 do not expand under the applied pressure.

The pouches 410, 420 can be manufactured as two separate discs and joined together around the linkage mechanisms 300 with a seam to reduce manufacturing costs. Preferably, the seam is made using a high frequency welding machine so as to be strong and resist rupturing.

In one embodiment, the pouches 410, 420 are fluid operated with fluid being supplied by means of conduits (tubes) 460 that can extend from the pouches 410, 420 to transmit the fluid. The conduits 460 can be flexible so as not to interfere with the patella and the tissues surrounding the joint as the knee joint is flexed and distracted. The fluid can be sterile water, saline solution, mineral oil, or any other appropriate fluid. A purge system can be incorporated to remove any bubbles in the system.

The height of each of the first and second upper femoral plateau members 250, 260 is independently controlled by a controller or the like. The controller can include one or more motors or the like that are operated to control the amount of fluid in each pouch 410, 420 and the height of the respective first and second upper femoral plateau members 250, 260. Operation of the motors results in fluid traveling through the conduits 460 into the pouches 410, 420 and this causes the fluid pressure to increase in the pouch 410, 420. Apposing forces are applied to the intermediate plates 430, 440 resulting in an increase in height of the upper femoral plateau plate 250, 260 relative to the base plates 220, 230 (first and second degrees of freedom (DOF)). This in turn causes the position of the femur 2 to change relative to the tibia 4 in the knee joint.

Figure 5:
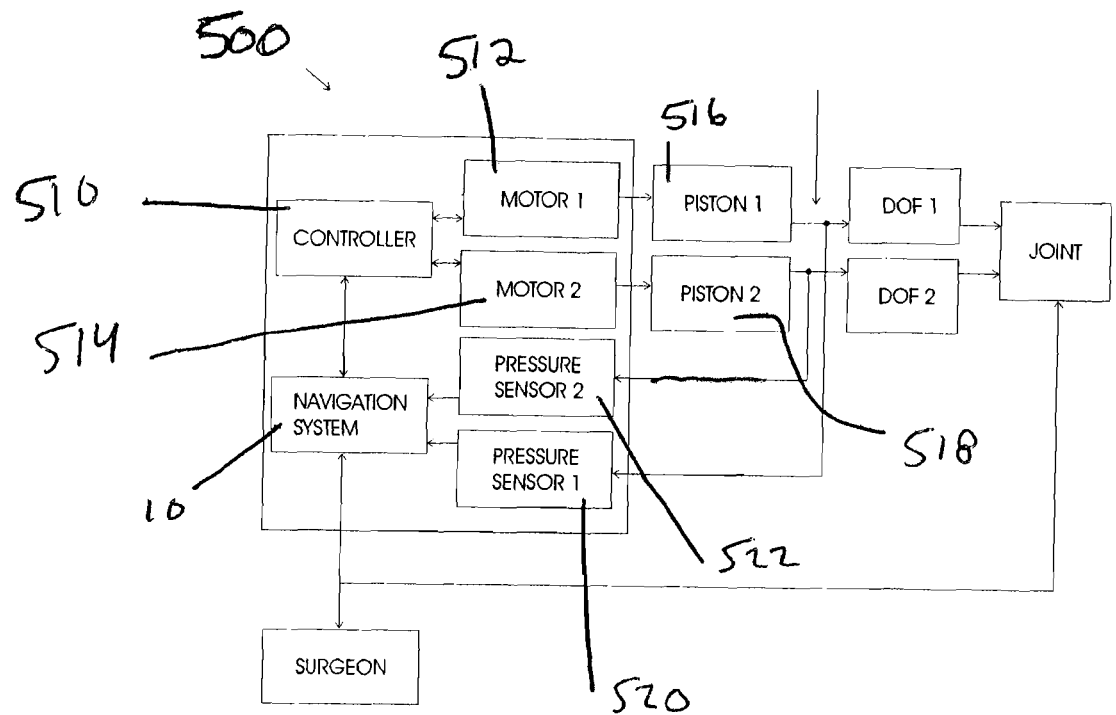
FIG. 5 is a schematic of one exemplary control system for controlling the movement of the distraction device of FIG. 2.

It will be appreciated that any number of different types of controllers, actuators, devices, etc., can be used to cause a controlled change in the distraction device 200. For example, the height of each plateau can be independently controlled by the navigation system 10. FIG. 5 schematically illustrates one exemplary control system 500. The system 500 includes a controller 510 that is configured to control first and second motors 512, 514, each of which has an encoder or linear hall sensor that provides position feedback to the controller 510. The motors 512 and 514 can independently control pistons 516, 518, respectively. Pistons 516, 518 are preferably syringes (e.g., plastic medical syringes) or similar type device that interface with the motors 512, 514 that can be part of a syringe pump infusion system, similar to those commonly used in an operating room. The syringes are connected to tubes via 'T' valves and this allows the entire fluid system to remain enclosed and sterile. Preferably, the entire system, including the syringes, tubes and the distraction device itself is intended for single use and is disposable, avoiding sterilization concerns and costs.

Controlling the motors 512, 514 therefore controls the amount of fluid in each pouch 410, 420 and the height of the distractor plateaus. When each motor 512, 514 changes the position of the piston 516, 518 such that fluid exits the syringe, fluid travels through the tube 460 and into the pouch 410, 420. This causes the fluid pressure to increase in the pouch 410, 420. Apposing forces are applied to the intermediate plates 430, 440, resulting in an increase in height of the upper plateau relative to the base plate (DOF 1 and 2, degree of freedom, FIG. 5). This in turn causes the position of the femur 2 to change relative to the tibia 4 in the knee joint.

The position of the joint is monitored by the camera of the navigation station 10 through reference bodies 102, 112, as previously described. The surgeon can manipulate the joint, and these motions are tracked and displayed on the user interface 32. Pressure sensors 520, 522 connect to the tubes 460 via the 'T' joints and monitor the fluid pressure in real time. Through a precalibrated relationship, these pressure readouts are inputted into the navigation station and are displayed as forces to the surgeon on the user interface 32.

According to the present invention, the distraction device 200 and related components of the system are preferably calibrated. The relationship between fluid volume and distraction height is known by and from a previously performed calibration procedure. This relationship can also be measured or verified in the operating room using a calibration height block 550 (FIG. 6). The distraction device, such as device 200, can be inserted in a slot 551 of known height. This slot 551 can have a height of, for example, 10 mm. Once the distraction device 200 is inserted into the slot 551, the surgeon pushes on the system foot pedal and the navigation system 10 or other control mechanism automatically increases the distraction height until the plateaus come into contact with the inner walls of the slot 551. At this point, the fluid pressure begins to increases, and this increase is detected by the navigations system 10 through the pressure sensors 520, 522. The controller 510 then automatically stops the motors 512, 514, memorizing their position in the computer. Now the fluid volume that corresponds to the distraction height of slot 551 is known. This process can be repeated if desired for another slot 552 of different height. Thus, the relationship between fluid volume (or motor position) and distraction height is known for at least one or two distraction heights. Thus by interpolation or extrapolation, the system determines the relationship between height and fluid volume. The general shape of the distractor height vs. fluid volume relationship can also be pre-determined, and can then be "zero'ed" or references with respect to the actual fluid volume in each syringe (or motor position) using the reference values of the height and volume measures during the calibration process described above. The relation between fluid volume and motor position is a linear one since the syringes or pistons are of a constant diameter.

The relationships between fluid volume, distraction height, measured pressure, and applied force can be precalibrated. These relationships can be a linear or non-linear one. If the relationships are non-linear, the measured fluid pressure and volume can be used to control the distraction height, through a function, such as $H=H_0+f(V, P)$, where X is an initial height, V is the volume of fluid, and P is the measured fluid pressure, and $f$ is a known pre-established function. That is to say, the relationship of height and fluid volume can be dependent on the pressure measured by the system, and vice versa. This can be evident if the pouch is of a deformable one, and as the applied force on the plateau is increased, the height of the plateau decreases even though the volume is held constant by the motors 512, 514 in the controller. This decrease in height is due to the deformation or expansion of the pouch under the applied pressure. Thus if the pressure increases, using the above relationship, the control system can increase the volume of fluid in each pouch 430, 440 to compensate for pouch deformation and keep the plateau height constant. The pre-measured relationships can also be used to calculate the applied force acting on the pouches 430, 440: $F=F_0+f(V, P)$. That is to say, the relationship between the pressure measured by the system and the applied force is dependent on the volume of fluid in the distraction device 200. This relationship is useful for compensating for effects in pressure measurements. For example, as the volume of fluid in the pouch 430, 440 increases, the pressure can also increase even if there is no force acting on the plateau. This increase in force could be due to the expansion of the pouch 430, 440, which requires energy in the form of a pressure. Therefore, using the predetermined relationship, it is possible to account for and cancel out this phenomena of fluid pressure increase with no increase in applied force, since we have measured relationship of pressure, volume, and applied force. Thus, it is possible to display to the surgeon the amount of force acting on each plateau. Note that other means of force measurement can also be employed such as strain resister force measurement devices, contact film pressure-sensor based devices, or any other form of force measurement known in the art.

As previously mentioned, the distraction device 200 can be used as a tool in a simulation package and in particular, it can be used in a process that simulates the relationship between at least one implant and a reference body, such as a bone, and more particularly, the relationship between first and second implants (femur and tibial) over a desired range of movement. In this manner, the present invention is related to a system and method for calculating and displaying a virtual implant and its movement relative to another body, such as another virtual implant or bone.

FIG. 7 shows schematically in a lateral view the planned position of a virtual femoral implant 600 and virtual tibial implant 610, the femoral 2 and tibial 4 bones, and the distractor 200 for a single compartment of the knee. It will be appreciated and understood that the term "virtual implant" refers to a representation of the implant that can be displayed on the computer screen and can be manipulated and considered when performing the relevant calculations and analysis; however, it does not physically exist.

More particularly, the three dimensional surfaces of the virtual implants 600 and 610 are known and are stored in a database of different implants in the navigation system memory as three dimensional models. These models can be point or mesh based models or parametric surface models, or any other type of model known. Thus, the three dimensional models of the virtual implants 600, 610 can be displayed on the computer screen (display) and can be manipulated (e.g., moved in space), with the change in position of the virtual implants 600, 610 being readily observed in real time on the computer screen. In addition, the three dimensional models of the virtual implants 600, 610 can be displayed on the screen in combination and in relation to a real physical object, such as a bone.

Each model of the virtual implants 600, 610 has its own coordinate system. From the initial planning, the transformation relating the positions of each virtual implant coordinate system to the position of the respective bone coordinate system is known. This initial implant plan is a flexible one and can be adjusted by the surgeon.

After the tibial cut has been made and an initial tibial and femoral implant planning has been performed, including the tibial insert size, the distractor size can be adjusted and is inserted into the joint. The base of the distractor can be fixed to the tibia and its position can be stored relative to the tibia, by for example digitizing the base with the point probe tip 124. The shapes of the surfaces of the plateaus, along with their positions relative to the base plate can also be known and stored in the computer memory as three dimensional geometrical files.

The distraction height can be determined by the navigation system 10 such that contact is simulated between the virtual components. In other words, the distraction device 200 is manipulated using the linkage mechanisms 300 such that the virtual components (e.g., virtual femoral implant and the virtual tibial implant) are in contact with one another so as to permit the two virtual components to remain in contact with one another but can also slidingly move with respect to one another. The navigation system 10 communicates to the controller 510 to automatically position each plateau 250, 260 to the correct height so as to position the virtual components in the desired location where the two are in contact with one another (bodies rest against each other). These heights can be determined statically or in real-time based on the relative position of the femur 2 and tibia 4 in 3D, in a closed control loop 500 (FIG. 5) in which the inputs are the relative knee joint bone positions (e.g., positions of femur 2 and tibia 4) and the outputs are the distraction heights. In this loop 500, the theoretical contact position of the virtual femoral and tibial components is solved and computed based on the 3D shapes and relative positions of the virtual femoral and tibial components, automatically adjusting the distraction height in each compartment such that the actual bone positions (actual positions of femur 2 and tibia 4) and the theoretical contact positions for the virtual components converge. The virtual contact between the virtual implants (p, FIG. 7) in a particular zone can be either a point, a collection of points, a curve or an area depending on the geometry and the level of conformity of the implant designs and the type of models used.

It will therefore be appreciated that the present system is configured so that the surgeon can view a single display or screen which not only contains images of the femur 2 and the tibia 4 and the relative positions thereof, as well as the distraction device 200, but also contains images of the virtual implants. Preferably, the virtual implants are readily and visually distinguishable from the other components, such as the femur 2, tibia 4 and distraction device 200, and are trackable in real time on the screen as the relative positions of the femur 2, tibia 4 and the device 200 are varied. For example, the virtual implants or at least outlines thereof can be illustrated in different colors or illustrated using different techniques, such as indicating the outlines thereof with dashed lines or the like as shown in FIG. 7. In this way, the surgeon can readily distinguish the relative positions of the two implants and more importantly, if the two are contact with one another. Since the system is designed to display the images in real time, as the surgeon moves one bone relative to the other, such as moving the tibia 4 relative to the femur 2, the movement of the virtual implants can be monitored and in particular if the two remain in contact with one another, etc. The relative movements of the distraction device 200 can also be tracked and observed during this movement.

In another aspect of the present invention, the simulation package/software includes a penetrating collision detection algorithm. A collision detection algorithm can be used to detect when and where a collision or intersection between the virtual implants has occurred. It will be appreciated that during the movements of the tibia 4 and femur 2, a collision should not result between the two virtual implants since this is indicative of an undesirable situation or event. Collision detection algorithms are well known in the literature, and any number of the known algorithms can be employed. As an example, each time a measurement of the position of femoral bone relative to the tibial bone is made, a check can be made to detect if any portion of one of the virtual implants has intersected the other virtual implant. One method of accomplishing this is to check if any node or nodes of the first implant mesh surface have passed through the boundary of the second implant mesh surface. Surface normal vectors for each triangular facet can be stored in the geometrical implant data files to indicate which direction is internal or external to the implant volume. In order to increase the real-time performance capabilities of the system, a predictive algorithm could also be used.

In one embodiment, the algorithm checks which nodes of one implant are close or the closest to any of the nodes of the other implant, as defined by a threshold distance or number of points. A distance map between the two models can also be calculated in order to determine the geometrical relationships between the two implants. A multi-resolution approach can be used where the distance calculations are performed initially for only a few well distributed points contained on the implants, to calculate roughly in which area the contact will likely occur. Once the initial zone or zones are identified the resolution of the search can be increased progressively until the exact or near-exact collision point or area is detected. For example, the direction of motion of the implant can be calculated to predict the intersection location when the implants come in close proximity of one another.

FIG. 10 illustrates an exemplary geometrical implant file (mesh file) and in particular, FIG. 10 is a close-up (local view) of one of the two posterior condyles of the femoral implant. FIG. 10 illustrates the nodes points) and facets (triangles) that make up the femoral implant. It will be appreciated that this is merely one illustration of a geometrical implant file.

Alternatively, the relative positions of the bones can be used to help predict the likely location of the intersection area. For example, if the position of the virtual femoral implant is posterior with respect to the virtual tibial implant in comparison to the central or neutral (aligned) position, then the algorithm can begin searching for possible intersection locations in the posterior regions of the tibial implant. The flexion angle of the leg can also be used to predict what area of the condyles of the virtual femoral implant is likely to be in contact with the virtual tibial plateau. For instance, the algorithm can begin searching in the distal areas of the femoral implant when the flexion angle is near zero degrees, and in the posterior areas of the femoral implant when the flexion angle is near 90 degrees. The varus/valgus or internal/external rotation angles, or the gap heights, could also be used to identify which compartments are in contact (medial and lateral).

Figure 8A:
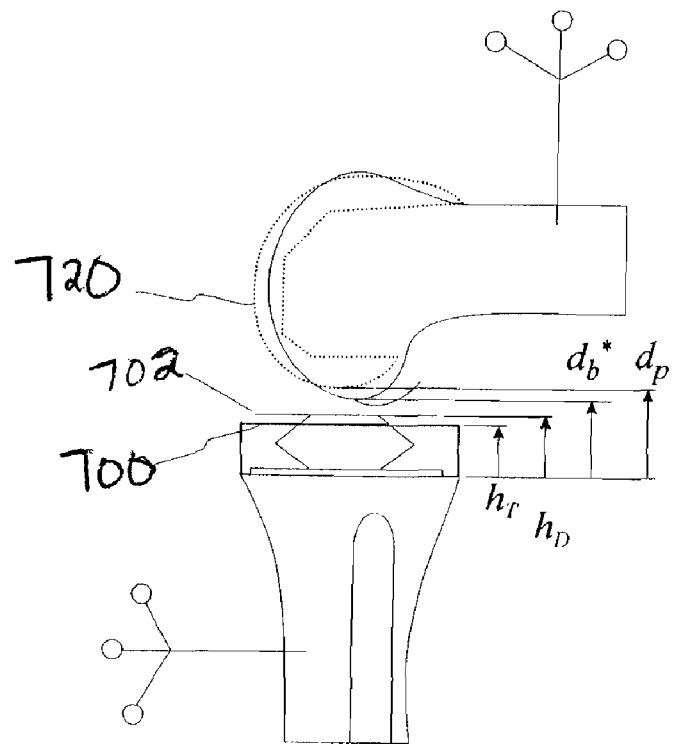
FIG. 8a is side view of the knee in flexion and illustrates a method of calculating a distraction height.

FIG. 8a illustrates one possible and simplified method for calculating the distraction height for one of the compartments of the knee. In this particular embodiment, the invention uses a knee distractor system where each upper distractor plateau is a flat plate 702 having an adjustable height $h_D$. Consider now the closest point on the femoral bone condyle to the distractor base plane (or tibial plateau cut). This point can be found by searching for the nearest point on the femoral bone model in the direction normal to the tibial plane. The normal distance from the tibial cut plane to this point is $d_b^*$. The location of this point on the tibial base plane is $\{x_T, y_T\}$ (not shown). Since the distractor plateau is flat and moves in a direction normal to the plateau, it is proper to assume that for this position and orientation of the femur with respect to the tibia, the femoral bone will contact the distractor plateau at this closest femoral point.

Similarly, the closest point on the virtual femoral implant to the distractor base plane can be found by searching for the nearest point in the virtual femoral implant model in the normal direction from the tibial cut plane. The normal distance from the tibial cut plane to this point on the prosthesis is $d_p^*$. The difference in these normal distances from the plane to the closest points $(d_p^* - d_b^*)$ is therefore $d_{pb}$.

Figure 8B:
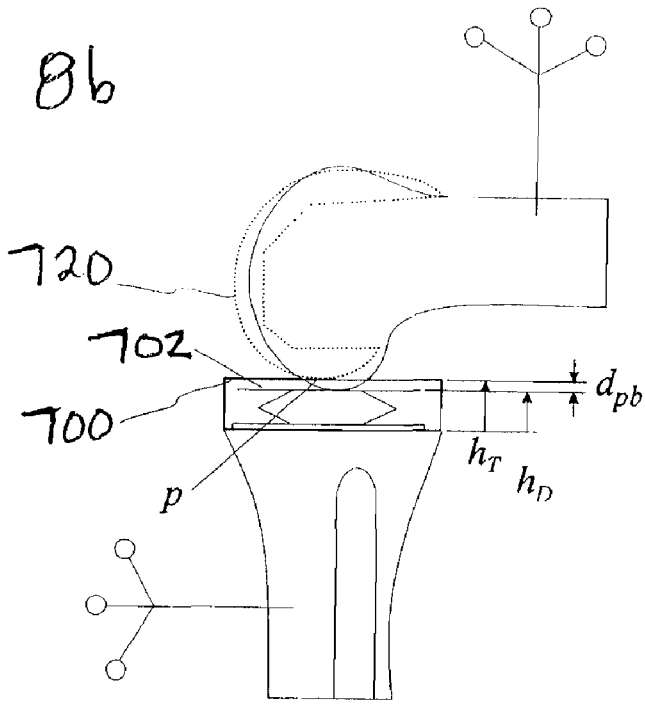
FIG. 8b is a side view of the knee in flexion with the virtual femoral implant in contact with and abutting against a virtual flat tibial plateau.

For the time being, the curvature of the virtual tibial implant surface is not considered but instead the tibial implant surface is considered also to be a flat plate 700 with fixed height $h_T$. Therefore, to simulate the virtual femoral implant 720 coming into contact and abutting against the simplified virtual flat tibial plateau (710 in FIG. 8b), the distraction device 200 would have to be positioned at a height of $h_D = h_T - d_{PB}$, for this particular orientation of knee flexion. Thus, the algorithm for positioning the distraction device 200 compensates for the differences in geometry between the virtual implant and actual bone surface.

This calculation and adjustment of the height of the distraction device 200 can be performed statically, or in real-time for different positions knee flexion, as measured by the localizing system. Thus, as the knee is flexed and extended, the system of the present invention re-calculates the corresponding closest normal distances to the femoral bone 2 and virtual prosthesis surfaces $d_b^*$–$d_p^*$ and adjusts the distractor height $h_D$ accordingly.

In accordance with one aspect of the present invention, a method of simulating a concave tibial implant using a flat distractor plateau is provided. Implant designs are usually more complex than simple flat plates, and they have curved surfaces with different radii of curvature. For instance, the convex femoral implant condyle surface is intended to rest in a "dish" shaped tibial plateau. Normally the radius of curvature of the tibial plateau is slightly greater than that of the femur 2 so that the femur 2 fits inside and is stable inside the plateau. Therefore, when the femur 2 is displaced in the anteroposterior direction relative to the tibia 4 for a given flexion angle (e.g., during an AP drawer test), the height of the femur 2 relative to the tibia 4 actually increases and decreases as the femoral condyle 3, 5 (FIG. 2) slides up and down inside the concaved tibial plateau surface, resulting in different tension applied to the ligaments surrounding the joint.

Referring now to FIGS. 9a-c, a tibial implant 730 having a concave plateau 732 is shown. As described previously, a collision detection algorithm can be used to detect when and where a collision or intersection between the virtual implants (pi) has occurred. A corresponding normal height from the distractor base to the intersection point can be defined, $d_p^*$. In the case of a distractor device having an upper plateau shaped as a flat plate, the height of the distractor device $h_D$ would be simply $d_b^*$ (normal distance to the closest point on the femoral bone condyle) calculated for this particular knee position.

In another aspect of the present invention, a method of simulating a concave implant using a concave distractor plateau is provided. In the case in which the distractor plateau is a curved shaped as shown in FIG. 9a, the height $h_t$ of the distraction device is the total height of the distractor device including the thickness of the plateau ($h_t$–$d_t$) at the contact point of the bone and distractor plateau. As mentioned previously, the position of the distractor base can be measured once it is inserted into the joint, and the height of the distractor device is known from the calibration procedure. The shape of the plateaus is also known and stored in the computer of the navigation system 10. Therefore, the thickness of the plateau ($h_t$–$d_t$) is known for any position with respect to the bones.

As the femur 2 moves with respect to the tibia 4, the algorithm runs in a loop continuously adjusting the distraction height such that a contact is simulated between the two virtual implants. Clearly, at some points in time during the movements, the virtual femoral implant will lift off the virtual tibial implant and contact will be lost. In this case the distractor device, such as device 200, can remain at its current position or even reduce its height and wait until the virtual femoral implant approaches the virtual tibial implant. The collision detection algorithm can then estimate in which area the contact is likely to occur and calculate the location of this contact more precisely as the virtual femoral implant moves closer to the virtual tibial implant. The computer in the navigation system 10 can then command the controller to begin moving in the relevant direction to the predicted height in anticipation of the predicted contact. This provides for a more responsive system and reduces the system delay or lag felt by the surgeon.

Conversely, at other times during the movement, the virtual femoral implant will overlap the tibial implant and the two bodies will share a common volume within each of their surfaces (in other words, the surface of one implant will penetrate the surface of the other implant). In this case, the control system can command the distractor device to push the femur 2 outside of the tibia 4, reducing the so called common volume (or the maximum 'distance of penetration') to a surface or point (or to a smaller distance of penetration that is under a reasonable threshold, such as about 1 mm). Thus, the contact between the virtual implants has returned to a realistic state (i.e. no overlap).

As the surgeon moves the femur 2 relative to the tibia 4, for example, from anterior to posterior as illustrated in FIGS. 9a-c, the algorithm monitors the change in position of the contact ($p_i$, $p_j$, $p_k$) and commands the control system to adjust the distraction height accordingly in real time. Thus, the surgeon feels the sensation of the femoral implant gliding over the tibial implant, while the height of the joint space gap changes. Thus, the surgeon can feel the overall tension and change in tension occurring in the ligaments and soft tissues surrounding the joint. In addition, the force sensors can display the forces occurring between the tibia 4 and femur 2 on the navigation system display.

Although the motion described above was in the anterior-posterior direction, as in an anterior posterior drawer test, the algorithm is not limited to this manipulation and is general and capable of handling other motions also. For example, the surgeon could move the femur 2 medially and laterally with respect to the tibia 4 and the algorithm would calculate the distraction heights accordingly. In the frontal plane the femoral condyles 3, 5 are also typically convex and the tibia 4 also typically concave, as in the lateral view (FIG. 8). In addition, other tests could be easily performed such as varus/valgus stress tests, rotational stability tests, Lachmann tests, pivot shift test, etc. In particular, during certain tests such as the varus/valgus stress or rotational stability tests, the gap or laxity between the virtual implants as measured by the camera and calculated navigation system can be displayed to the surgeon as the medial and lateral femoral condyles lift on and of the tibial plateaus. Based on these force and/or laxity data, the surgeon may wish to alter any of the initial planned position parameters of the femoral and tibial implants relative to the respective bones. This alteration in the planning can be performed on the navigation screen or with the system foot petal. The system will then input this new planning into the control algorithm and the surgeon can then re-examine the stability and kinematics of the knee while the distractor is simulating the new joint mechanics.

In yet another aspect of the present invention, a method of simulating a mobile bearing prostheses is provided. A mobile bearing, such as a rotating bearing or sliding bearing prostheses, can also be modelled and simulated. This can be accomplished by using an implant model that allows the surface to rotate or slide freely about a certain axis or plane defined with respect to the implant. For example, for rotating bearing tibial implants, the algorithm measures the position of the femoral component and then checks for intersections with the tibial component for multiple positions of rotation around the known and fixed axis of rotation, until a contact is detected. The femoral implant could push the tibial implant around the axis, always trying to reach the lowest point in the tibial plateau, where the interaction in intrinsically most stable. Sliding bearing prosthesis can also be modelled, by allowing the tibial component to slide linearly in the direction of the physical sliding axis. For planar sliding (meniscal) bearings, where the tibial insert is free to slide on the flat plateau of the metal tibial implant, the implant is free to slide in two directions in the plane. When there are compressive forces applied to the knee such that at least one condyle 3, 5 (FIG. 2) is in contact with the implant, the contact point would typically be at the lowest point of the mobile tibial plateau, since the tibial plateau would tend to center itself around the femoral condyle 3, 5. Thus, the distractor device would position itself at a height to maintain a contact at this lowest point. If the femoral implant begins to lift off from this lowest point on the tibial insert, the theoretical position of the tibial insert can slide on the plane, shifting the contact point to a higher position on the concaved tibial plateau surface in order to maintain contact with the femur.

In yet another aspect of the present invention, a method is provided for using a conventional or haptic robot as part of the overall simulation package of the present invention. Although the present method has been described using a distraction device, such as device 200, inserted in the knee joint, the present invention is certainly not limited to using a distraction device or the like and can be used with any device that is capable of controlling or limiting the contact or joint space between the femur 2 and tibia 4. For example, a distraction type device that is largely contained external to the joint can be used. A miniature bone mounted robot, or a larger conventional robot, or even a haptic robot can be used to manipulate the femur 2 and tibia 4 relative to one another in order to track and observe the relative positions of the virtual implants as described above.

In the case where the robot is a floor or table mounted robot, the femur 2 can be largely immobilised with respect to the table using a leg holder or similar device, and the robot end effector could be coupled to the tibia 4, using bone screws or less invasive means, such as a holder that wraps around the tibial shank. Alternatively, the femur 2 can be left free to move as it wishes, being only held by the hip and knee joints. The relative position of the bones 2, 4 can be measured using any method known in the art, such as magnetic, optical, acoustic, ultrasound, or mechanical arm localizers. The robot can then guide the motion of the tibia 4 with respect to the femur 2 such that the implants (virtual implants) are permitted to come into contact with one another, but cannot significantly overlap one another. In particular, semi-active robots known as active constraint robots or virtual fixtures or haptic robots can be used.

These systems allow the surgeon to move the robot end-effecter freely in certain directions or certain permitted areas, but they increase their "stiffness" in other directions or areas or portions of their workspace such that the surgeon is not allowed to enter in these forbidden areas. To illustrate this embodiment, the surgeon can hold the tibia and perform a knee flexion from extension to flexion. As the tibia 4 is flexing and rotating, the relative bone positions are being measured and the algorithm is predicting the virtual implant contact pattern, or in other words, it is calculating the minimal allowable joint space for each particular position of the femur relative to the tibia, and robotic device is controlling this gap space as the knee flexes. If the surgeon tries to push the tibia 4 into the femur 2, essentially reducing the joint space gap to a value smaller than the physical implants would allow if they were implanted in the planned positions, the robot would prevent the tibia 4 from moving in this direction. However, it can allow the tibia 4 to move tangential to the contact surfaces of the implant.

It will also be appreciated that according to one embodiment of the present invention, a method can be provided that does not use a model of the bone surface. In this variation of the invention, the joint mechanics and the contact between the implants can be simulated without having to acquire or to use a model of the actual bone surface. In the previous descriptions, the shape of the bone surface was used to calculate the desired height of the distractor device for each relative position of the knee bones. However, it is possible that the system could use only the simulated contact of the virtual implants, and that the distraction height can be driven by the difference in the distance between the virtual implants. For example, if there is lift-off detected by the camera between the virtual femoral implant condyle and the virtual tibial implant plateau, the navigation can send a command to the controller to lower the height of the distractor until it reaches a certain value, or until the virtual femoral implant condyle comes back into contact with the virtual tibial implant plateau. It is likely that when contact is re-established, it will be an overlap contact (i.e., surface penetration) because the distractor is positioned lower then the required. Surface penetrations between the two virtual implants can also happen at other times such as during the manipulations. Upon detection of a surface penetration, the navigation system 10 can send a command to the controller to increase the distraction height of the plateau. During this increase the depth of surface penetration is continuously monitored and the distraction height begins to stop increasing once the penetration depth begins to approach zero and the contact becomes a surface contact and not a volumetric one. Thus the distraction height is calculated based on the relative positions of the virtual implants and the error between the surfaces in order to maintain a surface contact, and the shape of the bone is not necessarily needed. In addition, the parameters of the controller can be optimized to improve the performance of the system, such and the pro-portional, integral, and differential (PID) parameters to have a very responsive and stable non-oscillatory output.

The following two examples illustrate yet again how the distraction device compensates for the difference in the shape of the actual femoral bone and the planned implants. Referring back to FIG. 7, it can be seen that the virtual femoral implant is distal to the bone surface in the area of the distal femoral condyle. In order for the virtual femoral implant to sit on the virtual tibial implant, the height of the gap space between the distal femoral condyle and the tibial cut must be equal to the height to the virtual tibial implant and plus the distance between the virtual femoral implant and the bone surface at the distal femoral condyle. Therefore the height of the plateau is higher that the height of the virtual tibial implant. FIG. 9b depicts the knee joint in flexion. In the region of contact, the posterior condylar surface of the virtual femoral implant is inside or anterior to the posterior condylar surface of the bone surface. The distraction height is determined from the models of the bone surfaces and the virtual implant models, and in this case, the height of the distractor plateau is positioned lower than the level of the tibial insert to compensate for the bone surface protruding from the virtual surface.

Once again, this dynamic process can be computed statically or in real time for the entire flexion range of motion. The surgeon can therefore flex and extend the knee with the distractor device in the joint, automatically adjusting the plateau heights as a function of the flexion angle and the position of the femur relative to the tibia as measured by the camera, and as a function of the planning of the virtual implants relative to the bone surface. In addition, the pressure sensors can monitor the fluid pressure and display a value indicative of the normal force to the surgeon on the screen as they are flexing and extending the knee. The position of the femur 2 relative to the tibia 4 is also displayed, along with the gap distances and laxity values. Laxity values can be determined by measuring and storing the maximum lift-off or gap distance values between the virtual femoral and tibial implants, as the surgeon manipulates the joint. These values can be measured at a particular point, for example, at the deepest point of the tibial plateau. According to the feeling of the surgeon and/or the force values displayed, he or she can adjust the planned position of the virtual femoral implant relative to the femur 2. For example, the surgeon can position the implant more distally on the femur 2 using the buttons on the navigation system's tactile screen if he feels that the knee is too lax in extension. The surgeon can therefore use the quantitative laxity measurements displayed on the screen in order to make an informed decision as to the implant plan.

Using the above method, it is possible to simulate precisely how "lax" or "over-stuffed" the joint feels based on the proposed implant planning. During a varus/valgus stress test, for example, when the medial and lateral condyles of the virtual femoral component lift off the virtual tibial component, the plateaus are at a height such that there is no femoral contact in the corresponding compartment and the surgeon can quantify the maximum laxities in each compartment. If the laxity is too large, the surgeon can change either the tibial insert height or the distal cut height, for example, and the distraction height will automatically readjust its position such that the new constraints are maintained. Similarly, in flexion the surgeon can adjust the rotation of the virtual femoral component and the distraction height in each compartment will change automatically such that the femur would sit on the tibia and the soft tissues would be tensed as would be the case if the actual components were installed in this position. The surgeon can evaluate any proposed component placement, continuously throughout the entire course of knee flexion, using both the laxity and the force readouts on the screen, and select the optimal one.

FIG. 9*a* depicts the knee still in flexion, with the femur 2 in a more anterior position relative to the tibia 4, in comparison to FIG. 9*b*. In this case the virtual contact point has moved anteriorly on the tibia and is now higher than in FIG. 9*b*, due to the particular shape of the virtual implants. Thus, as the surgeon pulls the tibia anteriorly relative to the femur, from its neutral position, the distraction height increases. Similarly, as the surgeon pushes the tibia 4 posteriorly relative to the femur 2, from its neutral position, the distraction height increases (FIG. 9*c*). Thus, the surgeon can push and pull and manipulate the tibia as in an AP drawer test, and feel the virtual implants gliding overtop of each other as the would if they were actually installed.

Once the planning has been validated by the surgeon using any one of the above techniques, the bone cuts (e.g., femoral bone cut) are made as usual using any number of conventional tools, such as a saw or robot, etc. The distractor device can now be used to revaluate the knee if desired, using the flat spacer blocks fastened to the plateaus, positioned over the femoral bone cuts.

Although the present invention has been described in the context of knee replacement surgery, the invention can also be applied to any other joint in the body, such as the hip, shoulder, elbow, etc., and also, for different procedures, such as partial resurfacing operations, including uni-condular knee replacement (for example, by using only one balloon mechanism). Hydraulic actuator system with motors, pistons, and DOF mechanisms can be replaced by any other actuation or robotic system. In addition, the means for moving the bones relative to one another can be in the form of a distraction device, as shown, or can be in another form, such as a robotic device, either of which can be based on hydraulic technology or some other type of technology that permits controlled movement of the device in at least one direction. The present system can be a calibrated system or an uncalibrated system, where the height is determined by a tracking system, using the distance from the bone surface.

EXAMPLE

In one exemplary application mentioned above, the present system is used in a knee replacement surgery and operation of the system includes the steps of: attaching a femoral reference body to the femur; attaching a tibial reference body to the tibia; building models of the femur and tibia; planning a tibial cut in the tibia; making and measuring the tibial cut; planning a tibial implant; registering a planned position of the tibial implant; planning an initial femoral implant based on a femoral model and optionally based on gap measurements; registering planned position of a femoral implant; adjust a size of a distraction device and inserting the distraction device in the joint; measuring the position of the femur relative to the tibia; adjusting the height of the distraction device accordingly and repeating the three above steps. The planned placement for the femoral and tibial implants are determined using virtual femoral and tibial implants that are graphically illustrated on the computer screen for viewing by the surgeon. Once the desired implant locations are determined in view of information received from measurements of the planned virtual implants, then bone cuts are made and the real physical femoral and tibial implants that were simulated by means of the virtual implants are installed in the joint.

The present invention thus provides a user friendly, visually pleasing system that in real time displays the spatial relationship between the bones and more importantly, the spatial relationship between the virtual implants to allow the surgeon to view a graphic display on the screen that represents all of these bodies of interest and the relative positions therebetween as one bone is moved relative to the other bone. The present system preferably requires no manual or mechanical adjustments by the surgeon and also reduces the dependence for requiring that the operating room have fully stocked real physical trail components for every combination of implant size.

It will be understood and as previously mentioned, the distraction device 200 or other similar device that moves one bone relative to the other bone is a means for simulating contact between the virtual implants and a means for maintaining the desired level of surface contact between the virtual implants. In other words, the operation (such as the height) of the distraction device is manipulated so that the first virtual implant (e.g., femoral implant) rests on and is in contact with a target surface of the second virtual implant (e.g., tibial implant).

In addition, during the performance of any test, such as a laxity test, the surgeon is of the opinion that excessive laxness is present for the virtual implants, then the surgeon can move the relative positions of the virtual implants, and then retest for laxity. Since the associated values of the laxity test can be displayed in real time on the computer screen along with an image of the virtual implants and the bones, the surgeon can easily in real time determine the optimal fit for the implants and then make the necessary bone cuts.

It will also be appreciated that the operator of the system can easily change which femoral or tibial implant has been initially selected and then perform the same series of tests to determine whether the new virtual implant pair offers any improvement over the prior one in terms of the surface contact between the virtual implants over a predetermined range of movement. For example, the type of implant can be changed in terms of its shape and/or size.

In this manner and based on the foregoing techniques and use of the foregoing tools, the surgeon can easily determine where to make the necessary bone cuts in order to properly locate the two implants without having to make the actual bone cuts. This is a marked improvement over the prior art systems and processes which necessitated that the bone cuts be made in order to assess how the two implants interact with one another.

While exemplary drawings and specific embodiments of the present invention have been described and illustrated, it is to be understood that the scope of the present invention is not to be limited to the particular embodiments discussed. Thus, the embodiments shall be regarded as illustrative rather than restrictive, and it should be understood that variations may be made in those embodiments by workers skilled in the art without departing from the scope of the present invention as set forth in the claims that follow, and equivalents thereof In addition, the features of the different claims set forth below may be combined in various ways in further accordance with the present invention.

What is claimed is:

1. A computer assisted orthopaedic surgery system for performing joint replacement of a joint that is defined by a first bone and a second bone comprising:
    means for tracking the position of the first bone relative to the second bone;
    means for planning a position of at least one virtual implant relative to the first tracked bone and at least one virtual implant relative to the second tracked bone; and
    means for controlling the relative position of the first and second tracked bones in at least one direction and with a controllable device that is physically coupled to the second bone and is operated such that relative positions of the bones behave in the manner as if an actual implant corresponding to the first and second virtual implants were installed according to the planned implant position, wherein the controllable device is a different structure relative to the actual implant and temporarily occupies a location which subsequently receives the actual implant.

2. A computer assisted orthopaedic surgery system for performing joint replacement of a joint that is defined by a first bone and a second bone comprising:
    a first device that is physically coupled to the second bone for moving the second bone in relation to the first bone, wherein the first device comprises a distraction device that is disposed between the first and second bones and is configured to engage and support the first bone; and
    a computer that permits an operator to plan a position of an implant by evaluating positions of first and second virtual implant components relative to the first and second bones, respectively; and a controller for controlling the position and movement of the first device coupled to the second bone such that actual positions of the first and second bones and theoretical contact positions for the first and second virtual implant components converge and contact is simulated between the first and second virtual implant components over a range of motion, wherein the controller is operatively connected to the distraction device and automatically adjusts a height of the distraction device such that contact is simulated between the first and second virtual implant components over the range of motion.

3. The system of claim 2, wherein the first bone is a femur and the second bone is a tibia and the first device is one of a distraction device and a robotic device that grips the second bone.

4. The system of claim 2, further including: a display operatively connected to the controller, wherein the controller generates three-dimensional images of the first and second bones and the first and second virtual components, the three-dimensional images being displayed on the display.

5. A computer assisted orthopaedic surgery system for performing joint replacement or resurfacing surgeries comprising:
    a computer that contains software that is adapted to measure and track a relationship between a first virtual implant component to be associated with a first bone and a second virtual implant component to be associated with a second bone and simulate the relationship of the two virtual implant components over a desired range of motion such that the two virtual implant components remain in contact with one another along outer surfaces thereof over the range of motion, the software receiving positional information for the two virtual implant components over the range of motion and then calculates the optimal locations for bone cuts so as to position the two virtual implants in the desired relationship where the outer surfaces are in contact with one another over the range of motion; and
    a distraction device that is coupled to the second bone and is disposed between the first and second bones and is configured to physically engage and support the first bone, wherein the system measures the position of the first bone relative to the second bone; and a controller that adjusts a height of the distraction device such that the first and second virtual implant components are positioned in locations where they are in contact with one another over the range of motion;
    wherein the distraction device has a pair of separate support members that each includes a bottom base plate, the bottom base plates being movably attached to one another to permit a distance between the separate support members to be varied, the support members being detached from one another along upper surfaces thereof.

6. The system of claim 5, wherein the first bone is a femur and the second bone is a tibia.

7. The system of claim 5, wherein the distraction device comprises a medical instrument, in the form of one of the support members, that includes a base; an upper member; and a linkage mechanism coupled to the base and the upper member and being operable to maintain the upper member in a variable fixed position that is substantially parallel to the base and spaced a predetermined, variable distance therefrom, wherein the linkage mechanism includes at least three linkage elements that are arranged at angles relative to one another such that when one link element opens, the other link elements open with at an equal angle resulting in the upper member being constrained to remain parallel to the base.

8. The system of claim 5, further including: a display operatively connected to the computer, wherein the computer generates three-dimensional images of the first and second bones and the first and second virtual components, the three-dimensional images being displayed on the display.

9. The system of claim 8, wherein the images of the first and second virtual implants are visually distinguished on the screen by either being displayed in a different color from the color of the images of the first and second bones or by displaying an outline of each of the virtual implants with broken lines.

10. The system of claim 5, further including: a robotic device that is movable in at least one direction and is coupled to the second bone for moving the second bone in at least one direction to permit tracking of the second bone relative to the first bone which is fixed in location, wherein the robotic device controls the relative positions of the tracked first and second bones such that kinematics of the joint behave as if an actual implant corresponding to the first and second virtual implant components was installed according to a planned implant position.

11. A computer assisted orthopaedic surgery system for performing implant surgery on a joint that is defined by a first bone and a second bone comprising:
a computer configured to plan the position and/or orientation of at least one first virtual implant with respect to the first bone and at least one second implant with respect to the second bone,
a three-dimensional position measuring device in communication with the computer, configured to measure the relative positions of the first and second bones; and
a first device selected from the group consisting of a distraction and a robotic device, each of which has at least one degree of freedom that is in communication with and is controlled by the computer, and is configured to limit the relative positions of the first and second bone so that the first virtual implant is prevented from overlapping the second virtual implant, wherein the computer is configured to communicate with the first device to automatically adjust a height of the first device to simulate movement between the first and second virtual implants over a range of motion in a manner in which the first virtual implant is prevented from overlapping the second virtual implant, wherein the first device is removable from its location between the first and second bones to permit insertion of an actual implant that has a first component for coupling to the first bone and a second component for coupling to the second bone.

12. The system of claim 11, wherein the first device is configured to measure the forces acting on it, wherein the measured forces are displayed on a screen of the computer.

13. The system of claim 11, wherein the computer can measure the relative displacements of the first and second bones at predefined points, and display the distances while the joint is manipulated.

14. The system of claim 13 wherein the displacements represent lift-off values and/or laxity values.

15. The system of claim 11, wherein the first device is a robotic device having a haptic arm of having at least 6 degrees of freedom.

16. The system of claim 1, wherein the first device has a pair of separate support members that are adjustably attached to one another but detached from one another along upper surfaces thereof to allow one support member to seat against one condyle and the other support member to seat against the other condyle.

17. The system of claim 16, wherein the first device has a planar lower surface and rests on a plateau cut made in the second bone.

18. The system of claim 17, wherein a pivotal connection between the separate support members is disposed above and out of a common plane that contains the lower surfaces of the pair of support members.

19. A computer assisted orthopaedic surgery system for performing joint replacement of a joint that is defined by a first bone and a second bone comprising:
means for tracking the position of the first bone relative to the second bone;
means for planning a position of at least one virtual implant relative to at least one of the first and second tracked bones; and
means for controlling the relative position of the first and second tracked bones in at least one direction and with a controllable device that is physically coupled to the second bone and is operated such that relative positions of the bones are spaced apart as if an actual implant corresponding to the virtual implant was installed according to the planned implant position, wherein the controllable device is a different structure relative to the actual implant and temporarily occupies a location which subsequently receives the actual implant.

20. A computer assisted orthopaedic surgery system for performing joint replacement of a knee joint that is defined by a femur bone and a tibia bone comprising:
means for tracking the position of the femur relative to the tibia;
means for planning on the computer a position of a virtual femoral implant on a model of the femur; and
means for automatically controlling via the computer and a controller the height of a distraction device placed in between the tibia and the femur, wherein the automatic controlling means is based at least partially on the difference in the distance between the surfaces of the virtual femoral implant and the model of the femur as determined at any particular degree of flexion.

21. The system of claim 20 wherein the distance is calculated in the direction normal to a cut made in the tibial to accommodate the distraction device.

22. The system of claim 20 wherein the model of the femur is a surface model.

23. The system of claim 20 wherein the model of the femur is based on at least one of the following data: point data, bone morphing data, medical image data.

24. The system of claim 20 wherein the computer also comprises means for planning a virtual tibial implant on a model of the tibia.

25. The system of claim 24 wherein the controlling means is also partially based on a fixed height of the planned tibial implant.

26. The system of claim 20 wherein the calculation is performed statically for different positions of knee flexion.

27. The system of claim 20 wherein the calculation is performed dynamically in real time for different positions of knee flexion, as measured by the tracking means.

28. The system of claim 20, wherein the controllable device is a different structure relative to the actual implant and temporarily occupies a location which subsequently receives the actual implant.

29. A computer assisted orthopaedic surgery system for performing joint replacement of a knee joint that is defined by a femur bone and a tibia bone comprising:
means for tracking the position of the femur relative to the tibia;
means for planning on a computer a position of a virtual femoral implant on a model of the femur; and
means for automatically controlling via the computer and a controller the height of a distraction device that is intended to be placed in between the tibia and the femur, wherein the automatic means for controlling the distraction device height is based at least partially on the distance between the surfaces of the virtual femoral implant and the virtual tibial implant, such that contact between the surfaces of the virtual femoral implant and the virtual tibial implant is obtained for at least a portion of the virtual implants.

30. The system of claim 29, wherein the distance between the surfaces of the virtual femoral implant and the virtual tibial implant is determined by the tracked position of the femur relative to the tibia.

31. The system of claim 29, wherein the distance between the surfaces of the virtual femoral implant and the virtual tibial implant is based on a most distal point on the virtual femur and fixed height value associated with the virtual tibial implant.

32. The system of claim 29 wherein the distraction device has one of flat and convex shaped upper plateau surfaces.

33. The system of claim 20 wherein, the difference in the distance between the surfaces of the virtual femoral implant and the model of the femur are determined with the knee in an extended position.

34. The system of claim 20 wherein, the difference in the distance between the surfaces of the virtual femoral implant and the model of the femur are determined with the knee in a flexed position.

* * * * *